United States Patent [19]

Malamas

[11] Patent Number: 5,045,544

[45] Date of Patent: * Sep. 3, 1991

[54] N'-ALKYL-SPIRO-ISOQUINOLINE-PYRROLIDINE TETRONES AND ANALOGS THEREOF USEFUL AS ALDOSE REDUCTASE INHIBITORS

[75] Inventor: Michael S. Malamas, Jamison, Pa.

[73] Assignee: American Home Products Corporation, New York, N.Y.

[*] Notice: The portion of the term of this patent subsequent to May 22, 2007 has been disclaimed.

[21] Appl. No.: 526,362

[22] Filed: May 21, 1990

[51] Int. Cl.$^5$ .................. A61K 31/44; C07D 417/14
[52] U.S. Cl. ................................ 514/278; 546/18; 546/142
[58] Field of Search .................... 546/18; 514/278

[56] References Cited

U.S. PATENT DOCUMENTS 4,927,831  5/1990  Malamas ........................... 514/278

OTHER PUBLICATIONS

Malen et al., Chem. Abst. 100-121065s (1984).
Brittain, Chem. Abst. 105-42767x (1986).

Primary Examiner—Cecilia Shen
Attorney, Agent, or Firm—Walter Patton

[57] ABSTRACT

This invention relates to N'-alkyl-spiro-isoquinoline-pyrrolidine tetrones and their pharmaceutically acceptable salts thereof, to processes for their preparation, to methods for using the compounds, and to pharmaceutical perparations thereof. The compounds have pharmaceutical properties which render them beneficial for the prevention or treatment of diabetes melitus associated complications.

9 Claims, No Drawings

N'-ALKYL-SPIRO-ISOQUINOLINE-PYRROLIDINE TETRONES AND ANALOGS THEREOF USEFUL AS ALDOSE REDUCTASE INHIBITORS

BACKGROUND OF THE INVENTION

This invention relates to N'-alkyl-spiro-isoquinoline-pyrrolidine tetrones and their pharmaceutically acceptable salts thereof, to processes for their preparation, to methods for using the compounds, and to pharmaceutical preparations thereof. The compounds have pharmaceutical properties which render them beneficial for the prevention or treatment of complications associated with diabetes mellitus.

The use of insulin and/or oral hypoglycemic agents in the treatment of diabetes mellitus has prolonged the life of many of these patients. However, their use has not had a demonstrable impact on the development of diabetic complications such as neuropathy, nephropathy, retinopathy, cataracts and vascular disease which accompany the underlying metabolic disorder. There is little question that chronic hyperglycemia plays a major role in the genesis of these complications, and that complete normalization of blood glucose would likely prevent most if not all complications. For a number of reasons, though, chronic normalization of blood glucose has not been achieved with the currently available therapies.

The long-term complications of diabetes develop in tissues where glucose uptake is independent of insulin. In these tissues, which include the lens, retina, kidney and peripheral nerves, the systemic hyperglycemia of diabetes is rapidly transposed into high tissular concentrations of glucose. In all of these tissues this excess glucose is rapidly metabolized by the sorbitol pathway. The intense diabetes-induced flux of glucose through this pathway appears to initiate a cascade of biochemical alterations which slowly progress to cell dysfunction and structural damage. Aldose reductase, the key enzyme in the sorbitol pathway, reduces glucose to sorbitol at the expense of the cofactor NADPH. In animal models of diabetes, compounds which inhibit aldose reductase have been shown to prevent the biochemical, functional and morphological changes induced by hyperglycemia. Early studies by J. H. Kinoshita and collaborators implicated aldose reductase in the etiology of diabetic cataracts. More recent studies have provided compelling evidence that aldose reductase also plays a significant role in the initiation of diabetic nephropathy, retinopathy and neuropathy (cf McCaleb et al, J. Diab. Comp., 2, 16, 1989; Robison et al, Invest. Ophthalmol. Vis. Sci., 30, 2285, 1989; Notvest and Inserra, Diabetes, 36, 500, 1987.

PRIOR ART

The closest prior art is allowed U.S. Ser. No. 357,563, filed May 26, 1989, which discloses the spiro-isoquinoline-pyrrolidine tetrones of formula

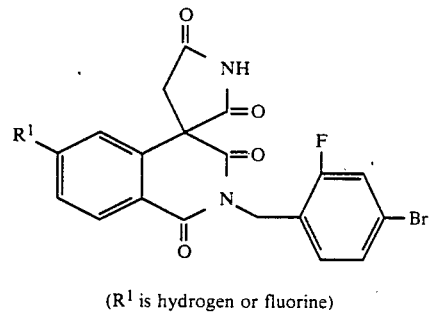

($R^1$ is hydrogen or fluorine)

useful as aldose reductase inhibitors for treating complications of diabetes and galactosemia.

SUMMARY OF INVENTION

The N'-alkyl-spiro-isoquinoline-pyrrolidine tetrones of the present invention are represented by formula (I):

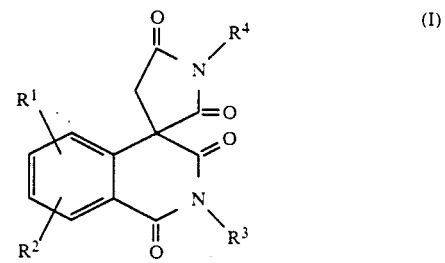

wherein $R^1$ and $R^2$ are independently hydrogen, alkyl containing 1 to 6 carbon atoms, halogen, lower alkoxy containing 1 to 6 carbon atoms, trifluoromethyl, nitro, aryl or aryl(lower alkyl)oxy wherein aryl contains 6 to 10 carbon atoms and lower alkyl contains 1 to 6 carbon atoms; $R^3$ is hydrogen, lower alkyl containing 1 to 6 carbon atoms, aryl, aryl(lower alkyl) or halogen substituted aryl(lower alkyl) wherein aryl contains 6 to 10 carbon atoms and lower alkyl contains 1 to 6 carbon atoms, or benzothiazole of structural formula

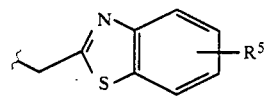

wherein $R^5$ is hydrogen, alkyl containing 1 to 6 carbon atoms, lower alkoxy containing 1 to 6 carbon atoms, trifluoromethyl, nitro, aryl or aryl(lower alkyl)oxy wherein aryl contains 6 to 10 carbon atoms and lower alkyl contains 1 to 5 carbon atoms; and $R^4$ is alkyl containing 1 to 12 carbon atoms, aryl, aryl(lower alkyl) wherein aryl contains 6 to 10 carbon atoms and lower alkyl contains 1 to 6 carbon atoms, acyl, carboalkoxy, or $-(CH_2)_nCO_2H$, $-(CH_2)_nOH$, wherein n is 1 to 6.

A more preferred group of compounds of the present invention are the compounds of formula (I) wherein $R^1$ and $R^2$ are independently hydrogen or halogen; $R^3$ is a mono- or dihalogen substituted aryl(lower alkyl) wherein aryl contains 6 carbon atoms and lower alkyl contains 1 to 3 carbon atoms, or benzothiazole of structural formula

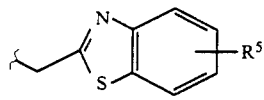

wherein $R^5$ is hydrogen, halogen or trifluoromethyl; and $R^4$ is alkyl containing 1 to 3 carbon atoms.

The most preferred compounds of the present invention are set forth below:

2-[(4-bromo-2-fluorophenyl)methyl]-1'-methyl-spiro[isoquinoline-4(1H), 3'-pyrrolidine]-1,2',3,5'(2H)-tetrone;

2-[(4-bromo-2-fluorophenyl)methyl]-1'-ethyl-spiro[isoquinoline-4(1H), 3'-pyrrolidine]-1,2',3,5'(2H)-tetrone;

2-[(4-bromo-2-fluorophenyl)methyl]-1'-ethyl-6-fluorospiro[isoquinoline-4(1H),3'-pyrrolidine]-1,2',3,5'(2H)-tetrone;

2-[[5-(trifluoromethyl)-2-benzothiazolyl]methyl]-1'-methylspiro[isoquinoline-4(1H),3'-pyrrolidine]-1,2',3,5'(2H)-tetrone;

1'-ethyl-6-fluoro-2-[[5-(trifluoromethyl)-2-benzothiazolyl]methyl]spiro[isoquinoline-4(1H),3'-pyrrolidine]-1,2',3,5'(2H)-tetrone.

The compounds of formula (I) all possess at least one asymmetric carbon atom, namely the spiro carbon atom at position 3' of the pyrrolidine ring. The compounds of formula (I) therefore exist, and may be isolated, in two or more stereoisomeric forms. This invention encompasses the compounds of formula (I) in racemic form or in any optically active form.

The N'-alkyl-spiro-isoquinoline-pyrrolidine tetrones can be prepared by the processes described hereinafter.

A method is provided for preventing or relieving diabetes mellitus associated complications in a diabetic mammal by administering to said mammal a prophylactic or alleviating amount of the compounds of formula (I). Such complications include neuropathy, nephropathy, retinopathy, keratopathy, diabetic uveitis, and cataracts.

The compounds of formula (I), when admixed with a pharmaceutically acceptable carrier, form a pharmaceutical composition which can be used according to the preceding method.

The N'-alkyl-spiro-isoquinoline-pyrrolidine tetrones of this invention may be administered to mammals, for example, man, cattle, or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the N'-alkyl-spiro-isoquinoline-pyrrolidine tetrones will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration, a 0.05–1.0% solution may be administered dropwise in the eye. The frequency of instillation varies with the subject under treatment from a drop every two or three days to once daily. For oral or parenteral administration a preferred level of dosage ranges from about 0.1 mg to about 1.0 mg per kilo of body weight per day, although aforementioned variations will occur. However, a dosage level that is in the range of from about 0.1 mg to about 1.0 mg per kilo of body weight per day is most satisfactory.

Unit dosage forms such as capsules, tablets, pills and the like may contain from about 5.0 mg to about 25.0 mg of the active ingredients of this invention with a pharmaceutical carrier. Thus, for oral administration, capsules can contain from between about 5.0 mg to about 25.0 mg of the active ingredients of this invention with or without a pharmaceutical diluent. Tablets, either effervescent or noneffervescent, can contain between about 5.0 to 25.0 mg of the active ingredients of this invention together with conventional pharmaceutical carriers. Thus tablets, which may be coated and either effervescent or noneffervescent, may be prepared according to the known art. Inert diluents or carriers, for example, magnesium carbonate or lactose, can be used together with conventional disintegrating agents for example, magnesium stearate.

The N'-alkyl-spiro-isoquinoline-pyrrolidine tetrones also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, *Physicians' Desk Reference*, 42 ed., Medical Economics Co., Oradell, N.J., U.S.A., 1988.

The aldose reductase inhibiting property of the compounds of this invention and the utilization of the compounds in preventing, diminishing and alleviating diabetic complications are demonstrable in experiments using galactosemic rats, see Dvornik et al., Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. An untreated galactosemic group was fed a similar diet in which galactose was substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by euthanization. Both the lens and sciatic nerve were removed, weighed and stored frozen for polyol determination.

(c) The polyol determination was performed by a modification of the procedure of M. Kraml and L. Cosyns, Clin. Biochem., 2, 373 (1969). Only two minor reagent changes were made: (a) the rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was substracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the N'-alkyl-spiro-isoquinoline-pyrrolidine tetrones of this invention show the property that they are active both in vitro and in vivo and diminish the accumulation of dulcitol in the lenses, sciatic nerves and diaphragm of rats fed galactose. The figures under L, N, and D represent the percentage decrease of dulcitol accumulation in the tissues of the lens, sciatic nerve, and diaphragm, respectively, for treated rats as compared to untreated rats.

ALDOSE REDUCTASE INHIBITORS

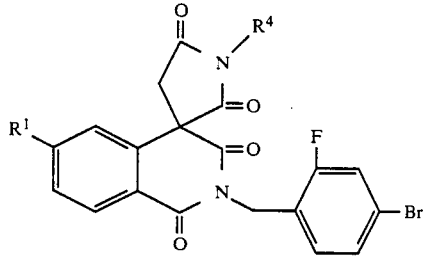

| | | % inhibition in vitro | % lowering dulcitol accumulation | | | |
|---|---|---|---|---|---|---|
| | | | dose | in vivo | | |
| $R^1$ | $R^4$ | $10^{-5}$ M | mg/kg | % L | % N | % D |
| H | —CH$_3$ | 0 | 0.5 | NS | 50 | 61 |
| | | | 1.1 | NS | 76 | 75 |
| | | | 10.2 | 31 | 95 | 94 |
| H | —CH$_2$CH$_3$ | 0 | 0.5 | NS | 37 | 56 |
| | | | 0.9 | NS | 65 | 73 |
| F | —CH$_2$CH$_3$ | 0 | 0.5 | NS | 19 | 65 |
| | | | 1.0 | NS | 74 | 84 |

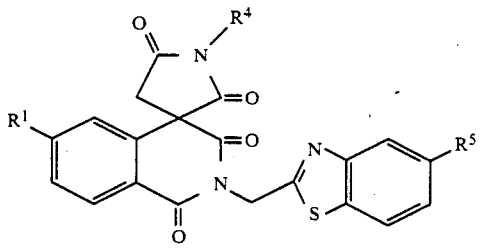

-continued
ALDOSE REDUCTASE INHIBITORS

| | | | % Inhibition Vitro | Dose mg/ kg/day | % Lowering Galactitol Accumulation | | |
|---|---|---|---|---|---|---|---|
| | | | | | In Vivo | | |
| $R^1$ | $R^4$ | $R^5$ | $10^{-6}$ M | | (%) L | (%) N | (%) D |
| H | CH$_3$ | CF$_3$ | 0 | 9.5 | NS | 82 | 100 |
| F | C$_2$H$_5$ | CF$_3$ | 0 | 10 | NS | NS | 59 |

PROCESS A

The N'-alkyl-spiro-isoquinoline-pyrrolidine tetrones of the present invention were prepared by the following reaction scheme:

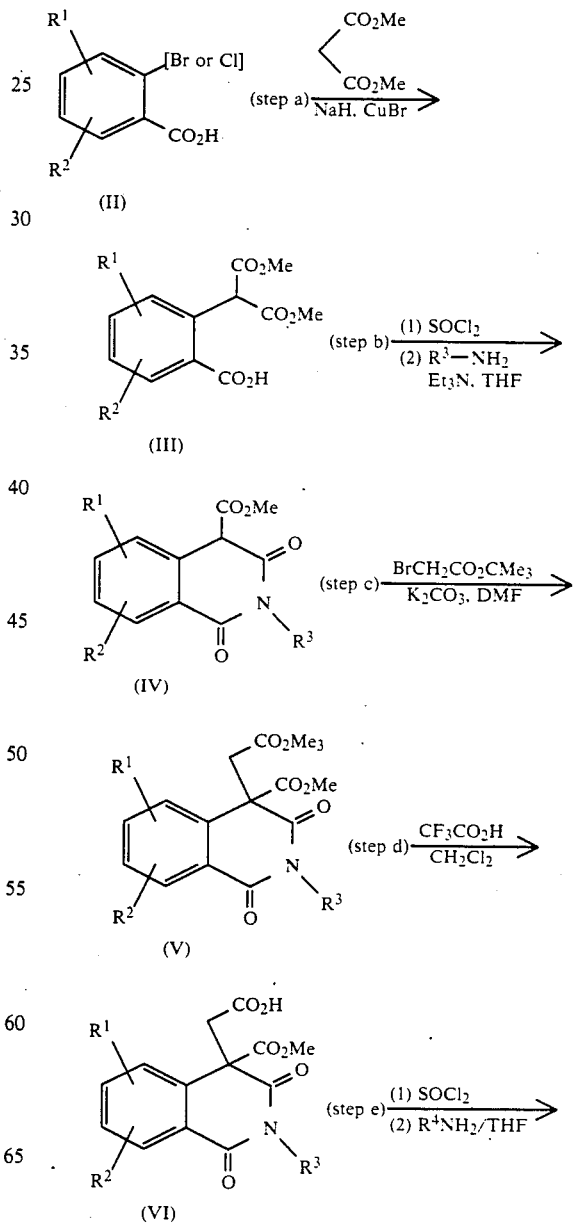

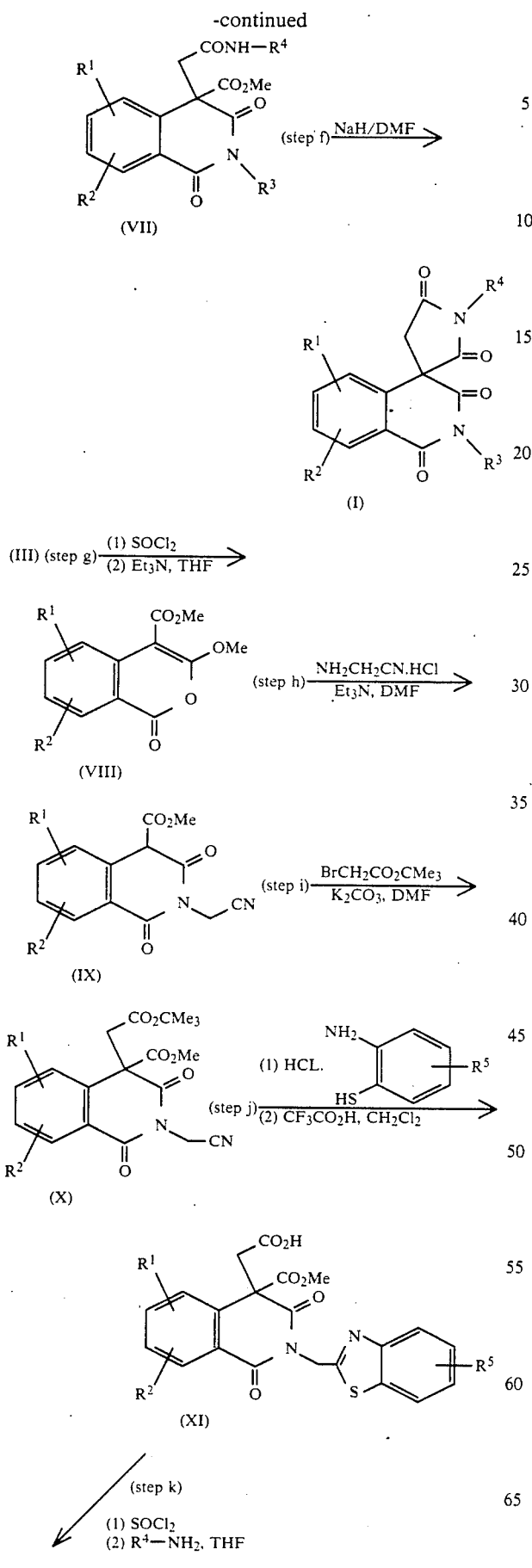
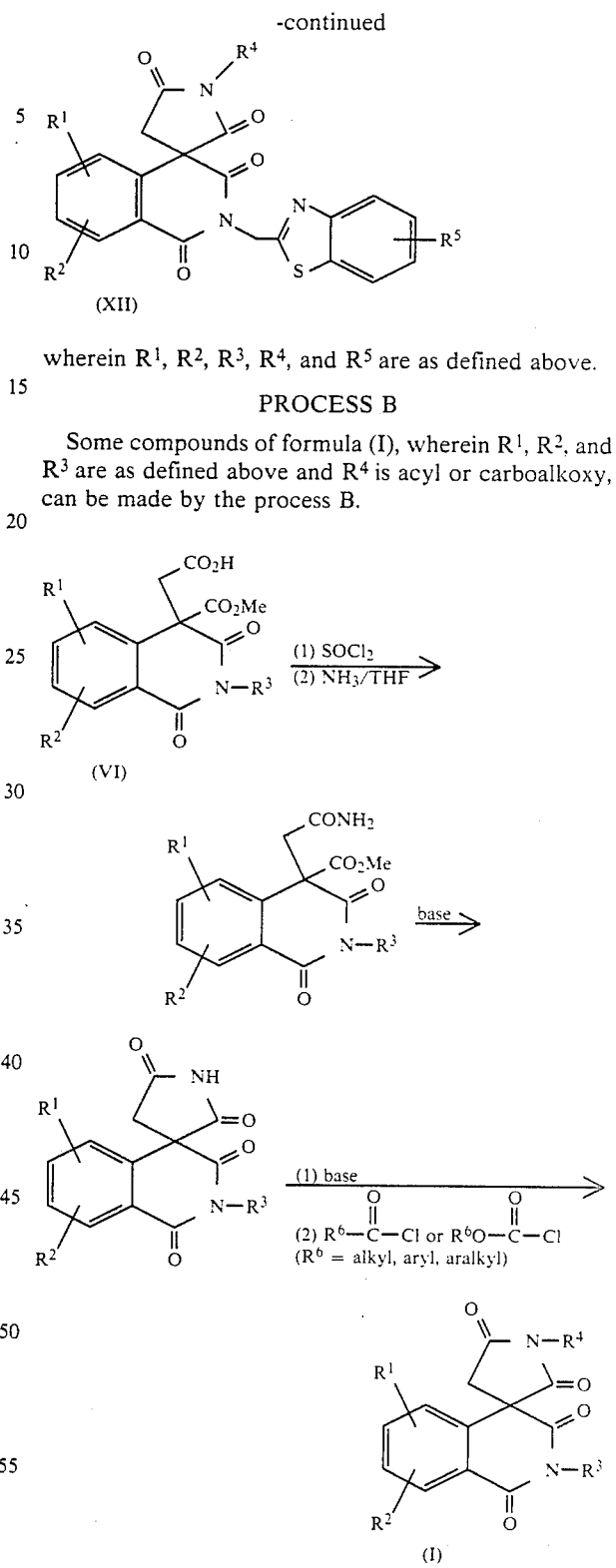

wherein $R^1$, $R^2$, $R^3$, $R^4$, and $R^5$ are as defined above.

PROCESS B

Some compounds of formula (I), wherein $R^1$, $R^2$, and $R^3$ are as defined above and $R^4$ is acyl or carboalkoxy, can be made by the process B.

wherein $R^1$, $R^2$, and $R^3$ are as defined above and $R^4$ is acyl or carboalkoxy.

Step a) Reacting either 2-bromobenzoic acid or 2-chlorobenzoic acid of formula (II) wherein $R^1$ and $R^2$ are as defined above with dimethyl malonate and NaH in the presence of a catalytic amount of CuBr to produce the propanedioic acid dimethyl ester of formula (III) wherein $R^1$ and $R^2$ are as defined above.

The 2-bromobenzoic acids or 2-chlorobenzoic acids of formula (II) required for the present invention are commercially available compounds or can be prepared by known methods.

Step b) The propanedioic acid dimethyl ester of formula (III) can be reacted with thionyl chloride under refluxing conditions to produce the corresponding acid chloride which upon treatment with an amine $R^3$—$NH_2$ in the presence of triethylamine in a conventional solvent which does not adversely influence the reaction, for example, tetrahydrofuran, can produce the compound of formula (IV) wherein $R^1$, $R^2$ and $R^3$ are as defined above.

Step c) The compound of formula (IV), wherein $R^1$, $R^2$ and $R^3$ are as defined above, is reacted with an inorganic base such as potassium carbonate in a conventional solvent which does not adversely influence the reaction, for example, N,N-dimethylformamide, and subsequent addition of the tert-butyl bromoacetate produces the compound of the formula (V), wherein $R^1$, $R^2$ and $R^3$ are as defined above.

Step d) The compound of formula (V), wherein $R^1$, $R^2$ and $R^3$ are as defined above, is hydrolyzed with an organic acid such as trifluoroacetic acid in a conventional solvent which does not adversely influence the reaction, for example, methylene chloride, to produce the compound of formula (VI), wherein $R^1$, $R^2$ and $R^3$ are as defined above.

Step e) The compound of formula (VI), wherein $R^1$, $R^2$ and $R^3$ are as defined above, can be reacted with thionyl chloride under refluxing conditions to produce the corresponding acid chloride, which upon treatment with $R^4$—$NH_2$ wherein $R^4$ is as defined above produces the amide of formula (VII), wherein $R^1$, $R^2$, $R^3$ and $R^4$ are as defined above. However, in the case when $R^4$=Me the initially formed amide (VII, when $R^4$=Me) cyclizes under these conditions to the final product (I, when $R^4$=Me).

Step f) The amide of formula (VII), wherein $R^1$, $R^2$, $R^3$ and $R^4$ are as defined above, is reacted with a base such as sodium hydride in a conventional solvent which does not adversely influence the reaction, for example, N,N-dimethylformamide, to produce the compound of the formula (I), wherein $R^1$, $R^2$, $R^3$ and $R^4$ are as defined above.

Step g) The propanedioic acid dimethyl ester of formula (III) can be reacted with thionyl chloride under refluxing conditions to produce the corresponding acid chloride which upon treatment with $Et_3N$ in a conventional solvent which does not adversely influence the reaction, for example, tetrahydrofuran, can produce the compound of formula (VIII), wherein $R^1$ and $R^2$ are as defined above.

Step h) The compound of formula (VIII), wherein $R^1$ and $R^2$ are as defined above, is reacted with aminoacetonitrile hydrochloride in the presence of $Et_3N$ in a conventional solvent which does not adversely influence the reaction, for example, N,N-dimethylformamide, produces the compound of the formula (IX), wherein $R^1$ and $R^2$ are as defined above.

Step i) The compound of formula (IX), wherein $R^1$ and $R^2$ are as defined above, is reacted with an inorganic base such as potassium carbonate in a conventional solvent which does not adversely influence the reaction, for example, N,N-dimethylformamide and subsequent addition of the tert-butyl bromoacetate produces the compound of formula (X), wherein $R^1$ and $R^2$ are as defined above.

Step j) The compound of formula (X), wherein $R^1$ and $R^2$ are as defined above, can be reacted with 2-aminothiophenols ($R^5$ is as defined above) under refluxing conditions in a conventional solvent which does not adversely influence the reaction, for example, ethyl alcohol, and subsequent treatment of the crude product with an organic acid such as trifluoroacetic acid in a conventional solvent which does not adversely influence the reaction, for example, methylene chloride, to produce the compound of formula (XI), wherein $R^1$, $R^2$ and $R^5$ are as defined above.

Step k) The compound of formula (XI), wherein $R^1$, $R^2$ and $R^5$ are as defined above, can be reacted with thionyl chloride under refluxing conditions to produce the corresponding acid chloride which upon treatment with $R^4$—$NH_2$ (wherein $R^4$ is as defined above) in a conventional solvent which does not adversely influence the reaction, for example, tetrahydrofuran, produces the compound of formula (XII), wherein $R^1$, $R^2$, $R^4$, and $R^5$ are as defined above. However, in the case that the initially formed amide does not cyclize under the reaction conditions, cyclization can be achieved in a similar manner as that of Step f.

The following examples further illustrate this invention:

EXAMPLE 1

2-[(4-Bromo-2-fluorophenyl)methyl]-1'-methylspiro[isoquinoline-4(1H), 3'-pyrrolidine]-1,2',3,5'(2H)-tetrone

Step A)

(2-Carboxyphenyl)propanedioic Acid Dimethyl Ester

To a rapidly stirred cold suspension (0° C.) of 2-bromobenzoic acid (30.0 g, 149.32 mmol), cuprous bromide (2.14 g, 14.93 mmol) and dimethyl malonate (300 mL) was added NaH (80% in mineral oil, 10.75 g, 358.37 mmol) over a 30 minute period, while a stream of dry $N_2$ was passed over the mixture. After the addition of the NaH had been completed, the mixture was stirred for 10 minutes at room temperature and 30 minutes at 70° C. (external oil bath temperature). At this point, the suspension had turned to a solid mass, which was dissolved in $H_2O$ (1000 mL). The aqueous layer was extracted with diethyl ether (3×500 mL) and was acidified with HCl (2N). The mixture was extracted with EtOAc and dried over $MgSO_4$. Evaporation gave an off-white solid which was recrystallized from $Et_2O$/hexane (−20° C.) to give a white solid (34.2 g, 90.9%).

$^1$H NMR (DMSO-$d_6$, 400 MHz): δ3.67 [s, 6H, —CH(CO$_2$CH$_3$)$_2$], 5.72 [s, 1H, —CH(CO$_2$CH$_3$)$_2$], 7.3 (d, J=7.76 Hz, 1H, Ar-H), 7.45 (dt, J=7.66 Hz, 1.12 Hz, 1H, Ar-H), 7.6 (dt, J=7.66 Hz, 1.45 Hz, 1H, Ar-H), 7.94 (dd, J=7.8 Hz, 1.33 Hz, 1H, Ar-H), 13.2 (s, 1H, —CO$_2$H).

IR (KBr, cm$^{-1}$): 3300–2700 (br), 1750 (s), 1730 (s), 1680 (s), 1430 (m), 730 (m).

MS (m/e): 252 (M$^+$), 220 (M$^+$—CH$_3$OH), 188 (M$^+$—2×CH$_3$OH).

Anal. Calcd.: C, 57.14; H, 4.80; Found: C, 57.05; H, 4.78.

M.P. 119°–120° C.

The following compound was prepared in substantially the same manner as that of Example 1, Step a):

(2-Carboxy-6-fluorophenyl)propanedioic Acid Dimethyl Ester $^1$H NMR (DMSO-d$_6$, 400 MHz): δ3.68 [s, 6H, (—CO$_2$Me)$_2$], 5.79 (s, 1H, Ar-H), 7.12 (dd, J=10.06 Hz, 2.61 Hz, 1H, Ar-H), 7.33 (dt, J=8.48 Hz, 2.64 Hz, 1H, Ar-H), 8.03 (dd, 8.77 Hz, 6.17 Hz, 1H, Ar-H).

IR (KBr, cm$^{-1}$): 3400–2700 (br), 1730 (s), 1680 (s), 750 (m).

MS (m/e): 270 (M$^+$), 238 (M$^+$—CH$_3$OH), 210 (M$^+$—CH$_3$OH, —CO), 151 (M$^+$—CH$_3$OH, —CO, —CO$_2$CH$_3$).

M.P. 121.5°–123.0° C.

Step B)

2-[(4-Bromo-2-fluorophenyl)methyl]-1,2,3,4-tetrahydro-1,3-dioxo-4-isoquinolinecarboxylic Acid Methyl Ester A mixture of (2-carboxyphenyl)propanedioic acid dimethyl ester (5.0 g, 19.84 mmol) and SOCl$_2$ (20 g) was refluxed for 1 and ½ hours. The volatiles were removed in vacuo and the acid chloride was dissolved in THF (20 mL). In a second flask were placed 4-bromo-2-fluorobenzylamine (4.67 g, 22.91 mmol), triethylamine (15.96 mL, 114.55 mmol) and THF (150 mL). The contents of the first flask were added to the second flask and the mixture was stirred for 30 minutes. The formed suspension was poured into H$_2$O (1000 mL), stirred for 10 minutes and acidified with HCl (2N). The mixture was extracted with EtOAc and the organic layer was dried over MgSO$_4$. Evaporation gave a yellowish solid which was recrystallized from acetone/ether/hexane (at −20° C.) to yield a white solid (6.01 g, 74.6%).

$^1$H NMR (DMSO-d$_6$, 400 MHz): δ[3.67, 3.99 (s, 3H, —CO$_2$CH$_3$, tautomeric)], [5.06 (q, J=15.4 Hz), 5.29 (s), 2H, N—CH$_2$—, tautomeric], 5.03 (s, 1H, —CHCO$_2$CH$_3$, tautomeric), 7.07–8.44 (m, 7H, Ar-H, tautomeric).

IR (KBr, cm$^{-1}$): 1675 (s), 1610 (s), 1490 (s), 7.95 (m).
MS (m/e): 405 (M$^+$), 373 (M$^+$—MeOH).

Anal. Calcd.: C, 53.22; H, 3.23; N, 3.45; Found: C, 52.91; H, 3.20; N, 3.27.

M.P. 149°–150° C.

The following compound was prepared in substantially the same manner as that of Example 1, Step b):

2-[(4-Bromo-2-fluorophenyl)methyl]-6-fluoro-1,2,3,4-tetrahydro-1,3-dioxo-4-isoquinolinecarboxylic Acid Methyl Ester $^1$H NMR (DMSO-d$_6$, 400 MHz): δ3.98 (s, 3H, —CO$_2$CH$_3$), 5.27 (s, 2H, —NCH$_2$—), 7.08 (t, J=7.95 Hz, 2H, Ar-H), 7.2 (m, 1H, Ar-H), 7.34 (m, 2H, Ar-H, —OH), 7.54 (m, 1H, Ar-H), 8.1–8.26 (m, 2H, Ar-H).

IR (KBr, cm$^{-1}$): 1680 (s), 1660 (s), 1610 (s), 785 (m).
MS (m/e): 423 (M$^+$), 391 (M$^+$—CH$_3$OH).

Anal. Calcd.: C, 50.97; H, 2.85; N, 3.30; Found: C, 50.86; H, 2.86; N, 3.33.

M.P. 157°–158° C.

Step C)

2-[(4-Bromo-2-fluorophenyl)methyl]-1,2,3,4-tetrahydro-4-(methoxycarbonyl)-1,3-dioxo-4-isoquinolineacetic Acid 1,1-Dimethylethyl Ester To a suspension of 2-[(4-bromo-2-fluorophenyl)methyl]-1,2,3,4-tetrahydro-1,3-dioxo-4-isoquinolinecarboxylic acid methyl ester (4.79 g, 11.58 mmol), K$_2$CO$_3$ (3.19 g, 23.16 mmol) in DMF (100 mL) was added tert-butyl bromoacetate (2.81 mL, 17.37 mmol). After stirring at 75° C. for 1 hour, the mixture was poured into H$_2$O, extracted with EtOAc and dried over MgSO$_4$. Evaporation and purification by flash chromatography (hexane/EtOAc, 4/1) gave a clear oil (5.69 g, 94.5%).

$^1$H NMR (DMSO-d$_6$, 400 MHz): δ1.04 [s, 9H, —C(CH$_3$)$_3$], 3.53 (s, 3H, —CO$_2$CH$_3$), 3.60 [dd, J=17.7 Hz, 2H, —CH$_2$CO$_2$C(CH$_3$)$_3$], 5.14 (s, 2H, NCH$_2$—), 7.17 (t, J=8.25 Hz, 1H, Ar-H), 7.36 (dd, J=8.36 Hz, 1.75 Hz, 1H, Ar-H), 7.6 (m, 3H, Ar-H), 7.77 (dt, J=7.2 Hz, 1.27 Hz, 1H, Ar-H), 8.19 (dd, J=8.25 Hz, 1.54 Hz, 1H, Ar-H).

IR (CHCl$_3$, cm$^{-1}$): 1720 (s), 1675 (s), 1360 (s), 765 (m).

MS (m/e): 520 (M+H)$^+$, 464 [M$^+$—C(CH$_3$)$_3$].

The following compound was prepared in substantially the same manner as that of Example 1, Step c):

2-[(4-Bromo-2-fluorophenyl)methyl]-6-fluoro-1,2,3,4-tetrahydro-4-(methoxycarbonyl)-1,3-dioxo-4-isoquinolineacetic Acid 1,1-Dimethylethyl Ester $^1$H NMR (DMSO-d$_6$, 200 MHz): δ1.1 (s, 9H, —CMe$_3$), 3.55 (s, 3H, —CO$_2$CH$_3$), 3.62 (d, J=1.75 Hz, 1H, —CH$_2$CO$_2$CMe$_3$), 3.75 (d, J=17.5 Hz, 1H, —CH$_2$CO$_2$CMe$_3$), 5.15 (s, 2H, —NCH$_2$—), 7.15 (t, J=8.2 Hz, 1H, Ar-H), 7.35 (d, J=8.2 Hz, 1H, Ar-H), 7.45–7.7 (m, 3H, Ar-H), 8.38 (dd, J=8.16 Hz, 5.70 Hz, 1H, Ar-H).

IR (KBr, cm$^{-1}$): 1750 (s), 1720 (s), 1675 (s).

M/S (m/e): 538 (M+H)$^+$, 481 (M$^+$+H, -tert-butyl).

Anal. Calcd.: C, 53.55; H, 4.12; N, 2.60; Found: C, 53.49; H, 4.00; N. 2.63.

Step D)

2-[(4-Bromo-2-fluorophenyl)methyl]-1,2,3,4-tetrahydro-4-(methoxycarbonyl)-1,3-dioxo-4-isoquinolineacetic Acid A mixture of 2-[(4-bromo-2-fluorophenyl)methyl]-1,2,3,4-tetrahydro-4-(methoxycarbonyl)-1,3-dioxo-4-isoquinolineacetic acid 1,1-dimethylethyl ester (5.19 g, 9.81 mmol), CH$_2$Cl$_2$ (100 mL) and CF$_3$CO$_2$H (20 mL) was stirred at room temperature for 5 hours. The volatiles were removed in vacuo and the residue was purified by flash chromatography on acid washed silica gel (5% H$_3$PO$_4$ in MeOH), to give a white solid (4.12 g, 90.5%).

$^1$H NMR (DMSO-d$_6$, 400 MHz): δ3.54 (s, 3H, —CO$_2$CH$_3$), 3.64 (dd, J=17.67 Hz, 2H, —CH$_2$CO$_2$H), 5.12 (dd, J=15.34 Hz, 2H, —NCH$_2$—), 7.14 (t, J=8.22 Hz, 1H, Ar-H), 7.3 (d, J=8.3 Hz, 1H, Ar-H), 7.5–7.6 (m, 3H, Ar-H), 7.76 (d, 7.4 Hz, 1H, Ar-H), 8.16 (d, J=7.8 Hz, 1H, Ar-H), 12.35 (s, 1H, —CO$_2$H).

IR (KBr, cm$^{-1}$): 3280 (m), 3500–2500 (br), 1750 (s), 1720 (s), 1675 (s), 1350 (s), 875 (m).

MS (m/e): 463 (M$^+$), 445 (M$^+$—H—OH).

Anal. Calcd. for C$_{20}$H$_{15}$BrFNO$_6$·0.2H$_2$O: C, 51.28; H, 3.30; N, 2.99; Found: C, 51.26; H, 3.48; N, 2.95.

M.P. 139°–140° C.

The following compound was obtained in substantially the same manner as that of Example 1, Step d):

2-[(4-Bromo-2-fluorophenyl)methyl]-6-fluoro-1,2,3,4-tetrahydro-4-(methoxycarbonyl)-1,3-dioxo-4-isoquinolineacetic Acid $^1$H NMR (DMSO-d$_6$, 400 MHz): δ3.56 (s, 3H, —CO$_2$CH$_3$), 3.6 (d, J=17.9 Hz, 1H, —CH$_2$CO$_2$H), 3.8 (d, J=17.9 Hz, 1H, —CH$_2$CO$_2$H), 5.1 (dd, J=15.5 Hz, 2H, —NCH$_2$—), 7.12 (d, J=8.23 Hz, 1H, Ar-H), 7.31

(dd, J=8.28 Hz, 1.68 Hz, 1H, Ar-H), 7.45 (dt, J=8.56 Hz, 2.5 Hz, 1H, Ar-H), 7.54 (dd, J=9.77 Hz, 1.89 Hz, 1H, Ar-H), 7.64 (dd, J=9.61 Hz, 2.46 Hz, 1H, Ar-H), 8.23 (dd, J=8.79 Hz, 5.81 Hz, 1H, Ar-H), 12.67 (brs, 1H, —CO$_2$H).

IR (KBr, cm$^{-1}$): 3400–2700 (br), 1745 (s), 1710 (s), 1670 (s), 770 (m).

MS (m/e): 481 (M$^+$), 405 (M$^+$—CO$_2$, —CH$_3$OH).

Anal. Cald.: C, 49.81; H, 2.93; N, 2.90; Found: C, 49.94; H, 3.03; N, 2.84.

M.P. 132°–133.5° C.

Steps E, F)

2-[4-Bromo-2-fluorophenyl)methyl]-1'-ethyl-spiro[isoquinoline-4(1H), 3'-pyrrolidine]-1,2',3,5'(2H)-tetrone A mixture of 2-[(4-bromo-2-fluorophenyl)methyl]-1,2,3,4-tetrahydro-4-(methoxycarbonyl)-1,3-dioxo-4-isoquinolineacetic acid (2.0 g, 4.31 mmol) and SOCl$_2$ (10 g) was refluxed for 1 hour. The volatiles were removed in vacuo and the acid chloride was dissolved in THF (10 mL). In a second flask was placed a freshly prepared saturated NH$_2$Et/THF solution (20 mL) and the contents of the first flask were added slowly. After 10 minutes the mixture was poured into H$_2$O, acidified with HCl (2N), extracted with EtOAc and the organic extracts were dried over MgSO$_4$. Evaporation gave a crude product which was dissolved in DMF (10 mL) and NaH (80% dispersion in oil, 129.3 mg, 4.31 mmol) was added portionwise. After 20 minutes the mixture was quenched with HCl (2N), extraced with EtOAc and dried over MgSO$_4$. Purification by flash chromatography (hexane/EtOAc, 4/1) and crystallization from ether/hexane (at −20° C.) gave a white solid (1.4 g, 70.7%).

$^1$H NMR (DMSO-d$_6$, 400 MHz): δ1.01 (t, J=7.2 Hz, 3H, —NCH$_2$CH$_3$), 3.4 (d, J=18.2 Hz, 1H, —CH$_2$CONEt—), 3.48 (q, J=7.2 Hz, 2H, —NCH$_2$CH$_3$), 3.52 (d, J=18.2 Hz, 1H, —CH$_2$CONEt—), 5.07 (s, 2H, —NCH$_2$—), 7.15 (t, J=8.23 Hz, 1H, Ar-H), 7.33 (dd, J=8.3 Hz, 1.76 Hz, 1H, Ar-H), 7.53 (dd, J=9.84 Hz, 1.9 Hz, 1H, Ar-H), 7.61–7.65 (m, 2H, Ar-H), 7.78 (dt, J=7.65 Hz, 1.43 Hz, 1H, Ar-H), 8.17 (dd, J=8.19 Hz, 1.49 Hz, 1H, Ar-H).

IR (KBr, cm$^{-1}$): 1720 (s), 1690 (s).

MS (m/e): 458 (M$^+$), 387 (M$^+$—CONEt—), 359 (M$^+$—CONEtCO—).

Anal. Calcd.: C, 54.92; H, 3.51; N, 6.10; Found: C, 54.92; H, 3.40; N, 6.13.

M.P. 153°–154° C.

The following compound was obtained in substantially the same manner as that of Example 1, Steps e, f):

2-[(4-Bromo-2-fluorophenyl)methyl]-1'-ethyl-6-fluorospiro[isoquinoline-4(H), 3'-pyrrolidine]-1,2',3,5'(2H)-tetrone $^1$H NMR (DMSO-d$_6$, 400 MHz): δ1.0 (t, J=7.17 Hz, 3H, —NCH$_2$CH$_3$), 3.41–3.48 (m, 4H, —CH$_2$CONEt—, —NCH$_2$CH$_3$), 5.05 (s, 2H, —NCH$_2$—), 7.14 (t, J=8.2 Hz, 1H, Ar-H), 7.33 (dd, J=8.2 Hz, 1.66 Hz, 1H, Ar-H), 7.47 (dt, J=8.6 Hz, 2.47 Hz, 1H, Ar-H), 7.52 (dd, J=9.8 Hz, 1.9 Hz, 1H, Ar-H), 7.72 (dd, J=9.8 Hz, 2.42 Hz, 1H, Ar-H), 8.23 (dd, J=8.8 Hz, 5.86 Hz, 1H, Ar-H).

IR (KBr, cm$^{-1}$): 1720 (s), 1695 (s).

M/S (m/e): 476 (M$^+$), 405 (M$^+$—CONEt—), 377 (M$^+$—CONEtCO—).

Anal. Calcd.: C, 52.85; H, 3.17; N, 5.87; Found: C, 52.71; H, 2.97; N, 5.84.

M.P. 185°–186° C.

2-[(4-Bromo-2-fluorophenyl)methyl]-1'-methyl-spiro[isoquinoline-4(H), 3'-pyrrolidine]-1,2',3,5'(2H)-tetrone A mixture of 2-[(4-bromo-2-fluorophenyl)methyl]-1,2,3,4-tetrahydro-4-(methoxycarbonyl)-1,3-dioxo-4-isoquinolineacetic acid (2.0 g, 4.31 mmol) and SOCl$_2$ (10 g) was refluxed for 1 hour. The volatiles were removed in vacuo and the acid chloride was dissolved in THF (10 mL). In a second flask was placed a freshly prepared saturated NH$_2$Me/THF solution (20 mL) and the contents of the first flask were added slowly. After 10 minutes the mixture was poured into H$_2$O, acidified with HCl (2N), extracted with EtOAc and the organic extracts were dried over MgSO$_4$. Evaporation and purification by flash chromatography (hexane/EtOAc, 4/1) gave an off-white solid which was recrystallized from ether/hexane (at −20° C.) to give a white solid (1.2 g, 62.5%).

$^1$NMR (DMSO-d$_6$, 400 MHz): δ2.93 (s, 3H, CH$_3$), 3.32 (s, 3H, —CO$_2$CH$_3$), 3.41 (d, J=18.2 Hz, 1H, —CH$_2$CONMe—), 3.54 (d, J=18.2 Hz, 1H, —CH$_2$CONMe—), 5.07 (s, 2H, —NCH$_2$—), 7.16 (t, J=8.3 Hz, 1H, Ar-H), 7.33 (dd, J=8.3 Hz, 2.5 Hz, 1H, Ar-H), 7.54 (dd, J=9.96 Hz, 2.07 Hz, 1H, Ar-H), 7.61–7.67 (m, 2H, Ar-H), 7.77 (dt, J=7.26 Hz, 1.45 Hz, 1H, Ar-H), 8.16 (dd, J=8.3 Hz, 1.87 Hz, 1H, Ar-H).

IR (KBr, cm$^{-1}$): 1710 (s), 1680 (s).

MS (m/e): 444 (M$^+$), 387 (M$^+$—CONMe—), 359 (M$^+$—CONMeCO—).

Anal. Calcd.: C, 53.95; H, 3.17; N, 6.29; Found: C, 53.69; H, 2.87; N, 6.21.

M.P. 78°–79° C.

EXAMPLE 2

2-[[5-(Trifluoromethyl)-2-benzothiazolyl]methyl]-1'-methylspiro[isoquinoline-4(1H), 3'-pyrrolidine]-1,2',3,5'(2H)-tetrone Step G)

3-Methoxy-1-oxo-1H-2-benzopyran-4-carboxylic Acid Methyl Ester

A mixture of (2-carboxyphenyl)propanedioic acid dimethyl ester (10.09 g, 39.68 mmol) and SOCl$_2$ (100 g) was refluxed for 2 hours. The volatiles were removed in vacuo and the crude product (acid chloride) was dissolved in THF (200 mL). Triethylamine (27.64 mL, 198.4 mmol) was added and the mixture was stirred for 30 minutes. The yellowish suspension was poured into HCl (1N, 1000 mL), extracted with EtOAc and the organic extracts were dried over MgSO$_4$. Evaporation and crystallization from acetone/ether/hexane (at −20° C.) gave a white solid (87.6 g, 94.4%).

$^1$H NMR (DMSO-d$_6$, 400 MHz): δ3.82 (s, 3H, —CO$_2$Me), 4.03 (s, 3H, —OMe), 7.42 (t, J=7.26 Hz, 1H, Ar-H), 7.8 (t, J=8.2 Hz, 1H, Ar-H), 7.9 (d, J=8.3 Hz, 1H, Ar-H), 8.1 (d, J=7.26 Hz, 1H, Ar-H).

IR (KBr, cm$^{-1}$): 1740 (C=O), 1685 (C=O).

MS (m/e): 234 (16, M$^+$), 206 (38.5, M$^+$—CO), 203 (12, M$^+$—OMe).

Anal. Calcd.: C, 61.59; H, 4.30; Found: C, 61.82; H, 4.29.

M.P. 129°–130° C.

The following compound was prepared in substantially the same manner as that of Example 1, Step g):

6-Fluoro-3-methoxy-1-oxo-1H-2-benzopyran-4-carboxylic Acid Methyl Ester $^1$H NMR (DMSO-d$_6$, 400 MHz): δ3.81 (s, 3H, —CO$_2$CH$_3$), 4.06 (s, 3H, —OCH$_3$), 7.27 (dt, J=8.3 Hz, 1H, Ar-H), 7.8 (dd, J=11.83 Hz, 2.49 Hz, 1H, Ar-H), 8.16 (dd, J=8.92 Hz, 6.2 Hz, 1H, Ar-H).

IR (KBr, cm$^{-1}$): 1750 (C=O), 1685 (C=O).

MS (m/e): 252 (24, M$^+$), 224 (54, M$^+$—CO).

Anal. Calcd.: C, 57.15; H, 3.60; Found: C, 57.19; H, 3.57.

M.P. 142°–143° C.

Step H)

2-(Cyanomethyl)-1,2,3,4-tetrahydro-1,3-dioxo-4-isoquinoline carboxylic Acid Methyl Ester To a solution of 3-methoxy-1-oxo-1H-2-benzopyran-4-carboxylic acid methyl ester (8.0 g, 34.19 mmol) in DMF (100 mL) was added aminoacetonitrile hydrochloride (6.32 g, 68.37 mmol) and the suspension was stirred until all the materials have dissolved. Triethylamine (14.3 mL, 102.57 mmol) was added and the mixture was stirred at 100° C. for 30 minutes, and then poured into H$_2$O, acidified with HCl (2N) and extracted with EtOAc. The organic extracts were dried over MgSO$_4$. Evaporation and crystallization from acetone/ether/hexane (at −20° C.) gave a yellowish solid (6.5 g, 73.7%).

$^1$H NMR (DMSO-d$_6$, 400 MHz): δ[3.7 (s), 3.98 (s), 3H, —CO$_2$CH$_3$, rotameric], [4.92 (s), 5.44 (s), 2H, —NCH$_2$CN, rotameric], 7.2–8.4 (m, 4H, Ar-H, rotameric).

IR (KBr, cm$^{-1}$): 3400 (OH), 1670 (C=O).

MS (m/e): 258 (20, M$^+$), 226 (43, M$^+$—MeOH), 199 (13, M$^+$—CO$_2$Me).

Anal. Calcd.: C, 60.47; H, 3.90; N, 10.85; Found: C, 60.27; H, 3.77; N, 10.69.

M.P. 169°–171° C.

The following compound was prepared in substantially the same manner as that of Example 1, Step h):

2-(Cyanomethyl)-6-fluoro-1,2,3,4-tetrahydro-1,3-dioxo-4-isoquinoline carboxylic Acid Methyl Ester Anal. Calcd.: C, 56.53; H, 3.28; N, 10.14; Found: C, 56.45; H, 3.22; N, 10.13.

M.P. 178°–179° C.

Step I)

2-(Cyanomethyl)-1,2,3,4-tetrahydro-4-(methoxycarbonyl)-1,3-dioxo-4-isoquinolineacetic Acid 1,1-Dimethylethyl Ester To a suspension of 2-(cyanomethyl)-1,2,3,4-tetrahydro-1,3-dioxo-4-isoquinoline carboxylic acid methyl ester (6.5 g, 25.19 mmol), K$_2$CO$_3$ (6.95 g, 50.38 mmol) and anhydrous DMF (100 mL) was added tert-butyl bromoacetate (6.1 mL, 37.79 mmol). After stirring at 85° C. for 3 hours, the mixture was poured into H$_2$O, acidified with HCl (2N) and extracted with EtOAc. The organic extracts were dried over MgSO$_4$. Evaporation and purification by flash chromatography on silica gel (hexane/EtOAc 4/1) gave a white solid (8.5 g, 90.7%).

$^1$H NMR (DMSO-d$_6$, 200 MHz): δ1.03 (s, 9H, —CO$_2$CMe$_3$), 3.58 (s, 3H, —CO$_2$CH$_3$), 3.64 (s, 2H, —CH$_2$CO$_2$—), 5.05 (s, 2H, —NCH$_2$CN), 7.64 (m, 2H, Ar-H), 7.78 (dd, J=7.4 Hz, 2.0 Hz, 1H, Ar-H), 8.24 (dd, J=8.2 Hz, 1.6 Hz, 1H, Ar-H).

IR (KBr, cm$^{-1}$): 1745 (C=O), 1730 (C=O), 1670 (C=O).

MS (m/e): 373 (38, M$^+$+H), 317 (100, M$^+$+H, —CME$_3$)

Anal. Calcd.: C, 61.28; H, 5.41; N, 7.52; Found: C, 61.61; H, 5.49; N, 7.13.

M.P. 48°–50° C.

The following compound was obtained in substantially the same manner as that of Example 1, Step i):

2-(Cyanomethyl)-6-fluoro-1,2,3,4-tetrahydro-4-(methoxycarbonyl)-1,3-dioxo-4-isoquinolineacetic Acid 1,1-Dimethylethyl Ester Anal. Calcd.: C, 58.46; H, 4.91; N, 7.18; Found: C, 58.65; H, 4.98; N, 7.08.

M.P. 133°–135° C.

Step J)

1,2,3,4-Tetrahydro-4-(methoxycarbonyl)-1,3-dioxo-2-[[(5-trifluoromethyl)-2-benzothiazolyl]methyl]-4-isoquinolineacetic Acid To a mixture of 3-amino-4-mercaptobenzotrifluoride hydrochloride (6.1 g, 26.2 mmol) and EtOH (150 mL) was added Et$_3$N (3.65 mL). After stirring for 10 minutes, 2-(cyanomethyl)-1,2,3,4-tetrahydro-4-(methoxycarbonyl)-1,3-dioxo-4-isoquinolineacetic acid 1,1-dimethylethyl ester (6.5 g, 17.47 mmol) was added and the mixture was refluxed for 15 hours, poured into H$_2$O, acidified with HCl (2N) and extracted with EtOAc. The organic extracts were dried over MgSO$_4$. Evaporation gave an oil (9.6 g) which was dissolved in CH$_2$Cl$_2$ (80 mL). Trifluoroacetic acid (20 mL) was added and the mixture was stirred at room temperature for 8 hours. The volatiles were removed in vacuo and the residue was purified by flash chromatography on acid washed (5%, H$_3$PO$_4$ in MeOH) silica gel to give a white solid (6.3 g, 73.3%).

$^1$H NMR (DMSO-d$_6$, 400 MHz): δ3.57 (s, 3H, —CO$_2$CH$_3$), 3.68 (dd, J=17.85 Hz, 2H, —CH$_2$CO$_2$H), 5.61 (s, 2H, —NCH$_2$—), 7.62 (m, 2H, Ar-H), 7.81 (m, 2H, Ar-H), 8.2 (dd, J=7.9 Hz, 1.04 Hz, 1H, Ar-H), 8.33 (dd, J=8.5 Hz, 0.92 Hz, 1H, Ar-H), 8.34 (d, J=0.83 Hz, 1H, Ar-H).

IR (KBr, cm$^{-1}$): 3200–2500 (CO$_2$H), 1750 (C=O), 1710 (C=O), 1670 (C=O).

MS (m/e): 492 (6, M$^+$), 448 (6, M$^+$—CO$_2$), 416 (62, M$^+$—CO$_2$, —MeOH).

Anal. Calcd.: C, 53.66; H, 3.07; N, 5.69; Found: C, 53.40; H, 3.01; N, 5.54.

M.P. 199°–201° C.

The following compounds were prepared in substantially the same manner as that of Example 1, Step j):

1,2,3,4-Tetrahydro-4-(methoxycarbonyl-1,3-dioxo-2-[(2-benzothiazolyl)methyl]-4-isoquinolineacetic Acid Anal. Calcd.: C, 59.43; H, 3.80; N, 6.60; Found: C, 59.37; H, 3.74; N, 6.43.

M.P. 189°–190° C.

6-Fluoro-1,2,3,4-tetrahydro-4-(methoxycarbonyl-1,3-dioxo-2-[[(5-trifluoromethyl)-2-benzothiazolyl]methyl]-4-isoquinolineacetic Acid Anal. Calcd.: C, 51.77; H, 2.76; N, 5.49; Found: C, 51.62; H, 2.97; N, 5.18.

M.P. 103°–105° C.

Step K)

2-[(5-Trifluoromethyl)-2-benzothiazolyl]methyl]-1'-methylspiro[isoquinoline-4(1H), 3'-pyrrolidine]-1,2',3,5'(2H)-tetrone

A mixture of 1,2,3,4-tetrahydro-4-(methoxycarbonyl)-1,3-dioxo-2-[[(5-trifluoromethyl)-2-benzothiazolyl)methyl]-4-isoquinolineacetic acid (2.0 g, 4.06 mmol) and $SOCl_2$ (20 g) was refluxed for 1 hour. The volatiles were removed in vacuo and the product (acid chloride) was dissolved in THF (10 mL). To a second flask was placed a freshly prepared, saturated $NH_2Me$/THF solution (20 mL) and the contents of the first flask were added slowly. After stirring for 10 minutes, the mixture was poured into $H_2O$ (500 mL) acidified with HCl (2N) extracted with EtOAc and dried over $MgSO_4$. Evaporation and purification by flash chromatography (hexane/EtOAc 2/1) gave a white solid (1.35 g, 80.3%).

$^1H$ NMR (DMSO-$d_6$, 400 MHz): $\delta$2.96 (s, 3H, N—$CH_3$), 3.43 (d, J=18.26 Hz, 1H, —HCHCO—), 3.56 (d, J=18.26 Hz, 1H, —HCHCO—), 5.56 (s, 2H, —NC$H_2$—), 7.66 (m, 2H, Ar-$\underline{H}$), 7.82 (m, 2H, Ar-$\underline{H}$), 8.20 (d, J=7.88 Hz, 1H, Ar-$\underline{H}$), 8.33 (m, 2H, Ar-$\underline{H}$).

IR (KBr, $cm^{-1}$): 1720 (C=O), 1700 (C=O), 1670 (C=O).

MS (m/e): 473 (100, M+).

Anal. Calcd.: C, 55.81; H, 2.98; N, 8.88; Found: C, 56.22; H, 2.97; N, 8.80.

M.P. 179°–180° C.

The following compound was prepared in substantially the same manner as that of Example 1, Step k):

1'-Ethyl-6-fluoro-2-[[5-(trifluoromethyl)-2-benzothiazolyl]methyl]spiro[isoquinoline-4(1H), 3'-pyrrolidine]-1,2',3,5'(2H)-tetrone

Anal. Calcd.: C, 54.66; H, 2.99; N, 8.31; Found: C, 54.97; H, 2.88; N, 8.35.

M.P. 154°–156° C.

We claim:

1. The compounds of structural formula (I)

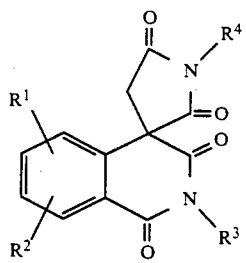

(I)

wherein $R^1$ and $R^2$ are independently hydrogen, alkyl containing 1 to 6 carbon atoms, halogen, lower alkoxy containing 1 to 6 carbon atoms, trifluoromethyl, nitro, aryl or aryl(lower alkyl)oxy wherein aryl contains 6 to 10 carbon atoms and lower alkyl contains 1 to 6 carbon atoms; $R^3$ is hydrogen, lower alkyl containing 1 to 6 carbon atoms, aryl, aryl(lower alkyl) or halogen substituted aryl(lower alkyl) wherein aryl contains 6 to 10 carbon atoms and lower alkyl contains 1 to 6 carbon atoms, or benzothiazole of structural formula

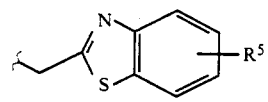

wherein $R^5$ is hydrogen, alkyl containing 1 to 6 carbon atoms, lower alkoxy containing 1 to 6 carbon atoms, trifluoromethyl, nitro, aryl or aryl(lower alkyl)oxy wherein aryl contains 6 to 10 carbon atoms and lower alkyl contains 1 to 5 carbon atoms; and $R^4$ is alkyl containing 1 to 12 carbon atoms, aryl, aryl(lower alkyl) wherein aryl contains 6 to 10 carbon atoms and lower alkyl contains 1 to 6 carbon atoms, acyl, carboalkoxy, or —$(CH_2)_nCO_2H$, —$(CH_2)_n$ OH, wherein n is 1 to 6.

2. The compounds according to claim 1 wherein $R^1$ and $R^2$ are independently hydrogen or halogen; $R^3$ is a mono- or dihalogen substituted aryl(lower alkyl) wherein aryl contains 6 carbon atoms and lower alkyl contains 1 to 3 carbon atoms, or benzothiazole of structural formula

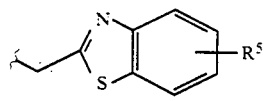

wherein $R^5$ is hydrogen, halogen or trifluoromethyl; and $R^4$ is alkyl containing 1 to 3 carbon atoms.

3. The compound according to claim 2
2-[(4-bromo-2-fluorophenyl)methyl]-1'-methylspiro[isoquinoline-4(1H), 3'-pyrrolidine]-1,2',3,5'(2H)-tetrone.

4. The compound according to claim 2
2-[(4-bromo-2-fluorophenyl)methyl]-1'-ethylspiro[isoquinoline-4(1H), 3'-pyrrolidine]-1,2',3,5'(2H)-tetrone.

5. The compound according to claim 2
2-[(4-bromo-2-fluorophenyl)methyl]-1'-ethyl-6-fluorospiro[isoquinoline-4(1H,3'-pyrrolidine]-1,2',3,5'(2H)-tetrone.

6. The compound according to claim 2
2-[[5-(trifluoromethyl)-2-benzothiazolyl]methyl]-1'-methylspiro[isoquinoline-4(1H), 3'-pyrrolidine]-1,2',3,5'(2H)-tetrone.

7. The compound according to claim 2
1'-ethyl-6-fluoro-2-[[5-(trifluoromethyl)-2-benzothiazolyl]methyl]spiro[isoquinoline-4(1H), 3'-pyrrolidine]-1,2',3,5'(2H)-tetrone.

8. A pharmaceutical composition for preventing or relieving neuropathy, nephropathy, retinopathy, or cataracts in a diabetic mammal, which comprises an effective amount of claim 1 and a pharmaceutically acceptable carrier.

9. A method of preventing or relieving neuropathy, nephropathy, retinopathy, or cataracts in a diabetic mammal, which comprises administering to said mammal an alleviating or prophylatic amount of a compound of claim 1.

* * * * *